United States Patent [19]

Zacharias

[11] Patent Number: 4,656,869
[45] Date of Patent: Apr. 14, 1987

[54] METHOD OF MEASURING THE AMOUNT OF WATER FLOWING IN A CRUDE OIL PIPELINE

[76] Inventor: Ellis M. Zacharias, 11391 E. Tecumseh St., Tulsa, Okla. 74116

[21] Appl. No.: 747,924

[22] Filed: Jun. 24, 1985

[51] Int. Cl.[4] .................................. G01N 29/00
[52] U.S. Cl. ............................ 73/597; 73/61.1 R
[58] Field of Search ........................ 73/597, 61.1 R

[56] References Cited

U.S. PATENT DOCUMENTS

| | | | |
|---|---|---|---|
| 3,892,127 | 7/1975 | Cirulis et al. | 73/61.1 R |
| 3,973,430 | 8/1976 | Cirulis et al. | 73/597 |
| 4,059,987 | 11/1977 | Dowling et al. | 73/61.1 R |

*Primary Examiner*—Anthony V. Ciarlante
*Attorney, Agent, or Firm*—Head, Johnson & Stevenson

[57] ABSTRACT

A method of measuring the composition of an oil and water mixture flowing in a pipeline includes the steps of extracting a sample of the mixture from the pipeline, measuring the speed of sound transmission of the mixture which may be carried out either in the pipeline or in a portion of the extracted sample, separating the water from at least a portion of the extracted sample, measuring the speed of sound transmission of the sample of the mixture having the water separated therefrom, and comparing the determined speed of sound transmission of the mixture and the speed of sound transmission of the sample having water separated therefrom to determine the ratio of oil and water in the mixture.

9 Claims, 5 Drawing Figures

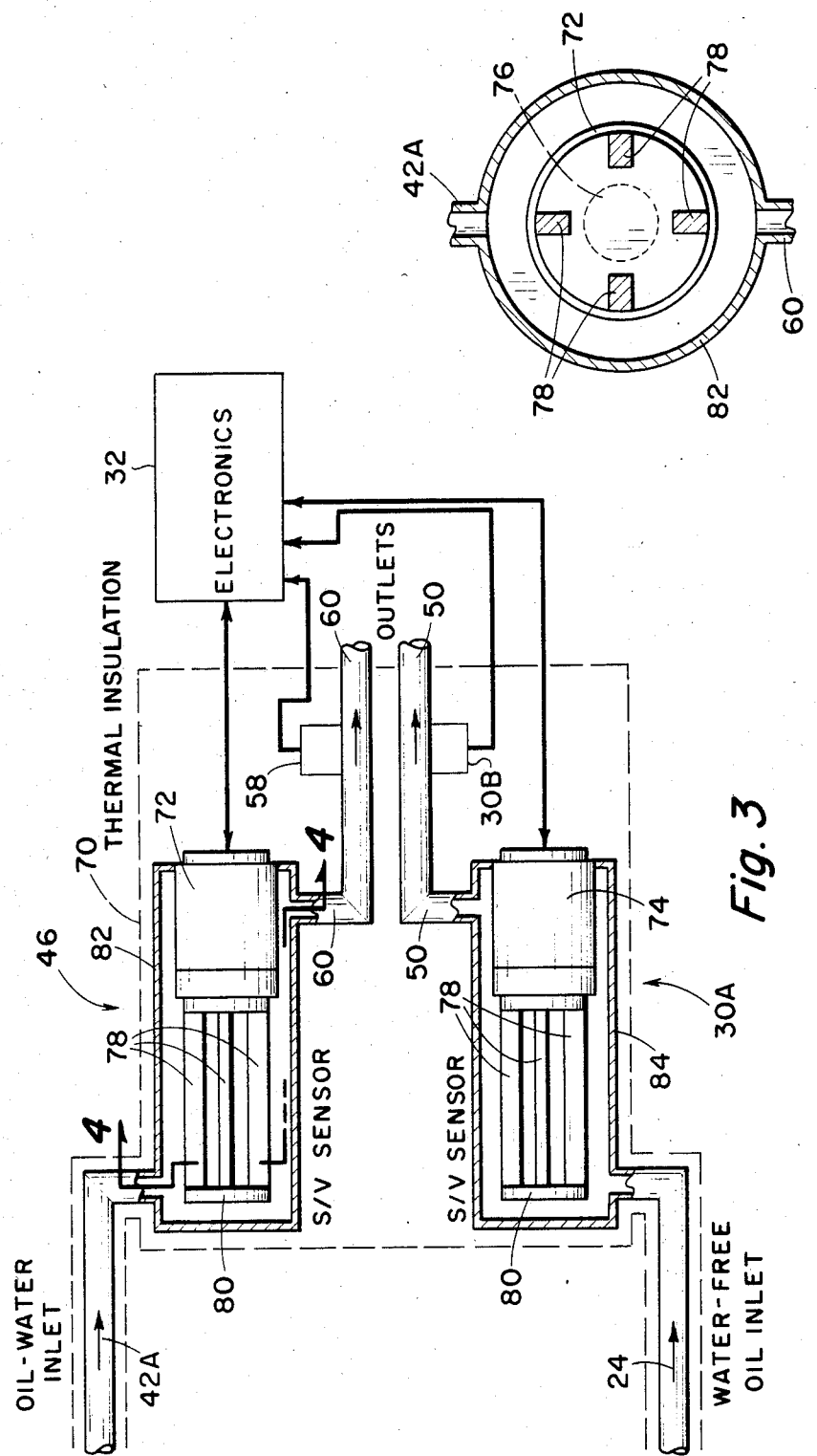

METHOD OF MEASURING THE AMOUNT OF WATER FLOWING IN A CRUDE OIL PIPELINE

SUMMARY OF THE INVENTION

A need exists for a better method of measuring the amount of water in an oil and water mixture, particularly in crude oil. The most common method of measuring oil/water ratios in commercial use is the measurement of the dielectric constant by means of a capacitance probe. However, capacitance probes are subject to coating by paraffin and other substances which render them inaccurate in a short period of time. Another scheme involves the laboratory analysis of samples, but this method is labor intensive, requires much time such as an hour or more to complete, and does not lend itself to continuous monitoring of fluid, such as crude oil flowing in a pipeline.

The present invention provides an accurate, essentially continuous, measurement of the water and oil ratios in a mixture, such as crude oil, flowing in a pipeline.

Others have provided concepts for measuring the ratio of oil and water in a mixture, such as U.S. Pat. No. 3,973,430, which is directed to a concept of measurement in a large volume of liquid, such as that contained in the ballast liquid carried by tankers and the effluent from refineries.

The present invention is directed towards the specific problem of monitoring the ratio of the water contained in a mixture with oil flowing in a pipeline. Most of the crude oil produced in the world today is transmitted from the areas of production to refineries by means of pipelines. It is expensive to transmit fluid over long distances by pipelines. Of more importance is the problem of custody transfer. Oil is customarily metered as it flows from a producing line to a customer, either a pipeline company or a refiner. Since oil is an expensive commodity it is important that it be accurately measured, and if it is mixed with water the customer pays for the water. If the ratio of oil and water is known, the water content can be deducted.

It is customary to remove as much as practically possible of the water near the point of production and to thereafter transmit only crude oil. However, the methods of removing water from crude oil on a large scale basis are not completely effective and variations in conditions can result in some water being carried as a mixture with the crude oil. Since compensation for delivery of crude oil is usually based on measurements made as the crude oil is flowing in a pipeline, it is extremely important to know accurately the amount of water making up the mixture. In addition, if through some inadvertence or accident, the ratio of water to oil in a mixture increases, it is exceedingly important for operators to be apprised of such information.

In the present invention a sample of the mixture flowing through a pipeline is taken either on a continuous basis or preferably on a frequent, timed cycle basis. The sample of the fluid mixture is passed through an oil/water separator wherein the water content is removed. The speed of sound transmission is then measured of the mixture of water and oil and independently, but preferably substantially simultaneously, of the oil have the water extracted therefrom. The separate speed of sound measurements are applied to electronics wherein by appropriate software the ratio of the oil and water in the mixture is determined. This detected ratio may be constantly displayed on the monitor and the data therefrom fed to be recorded are used in computer apparatus such as to compute the quantity of the oil being transmitted in the mixture.

In one embodiment the speed of sound transmission is measured directly in the pipeline and preferably, along with the temperature of the mixture. In a second, and more preferable embodiment, a sample of the mixture is taken and divided into two flow paths. In one flow path the speed of sound transmission of the mixture per se is taken and in another flow path the water is first extracted and the speed of sound transmission of the oil content is separately measured. The measurements are preferably practiced substantially simultaneously and preferably with separate instrumentation. In addition, the temperature of the measurements is important and in the second embodiment the mixture and the oil having the water extracted therefrom are preferably subjected to a heat exchange relationship so that the speed of sound measurements are made at substantially the same temperatures in both the mixture itself and in the mixture having the water extracted from it.

The invention will be more completely understood with reference to the following description and claims, taken in conjunction with the attached drawings.

DESCRIPTION OF THE DRAWINGS

FIG. 3 is an enlarged diagrammatic illustration of a portion of the apparatus employed for taking the speed of sound transmission measurements, the apparatus being shown in more detail.

FIG. 4 is a fragmentary cross-sectional view taken along the line 4—4 of one of the speed of sound transmission measurement devices of FIG. 3.

DETAILED DESCRIPTION OF THE EMBODIMENT

Figure 1:
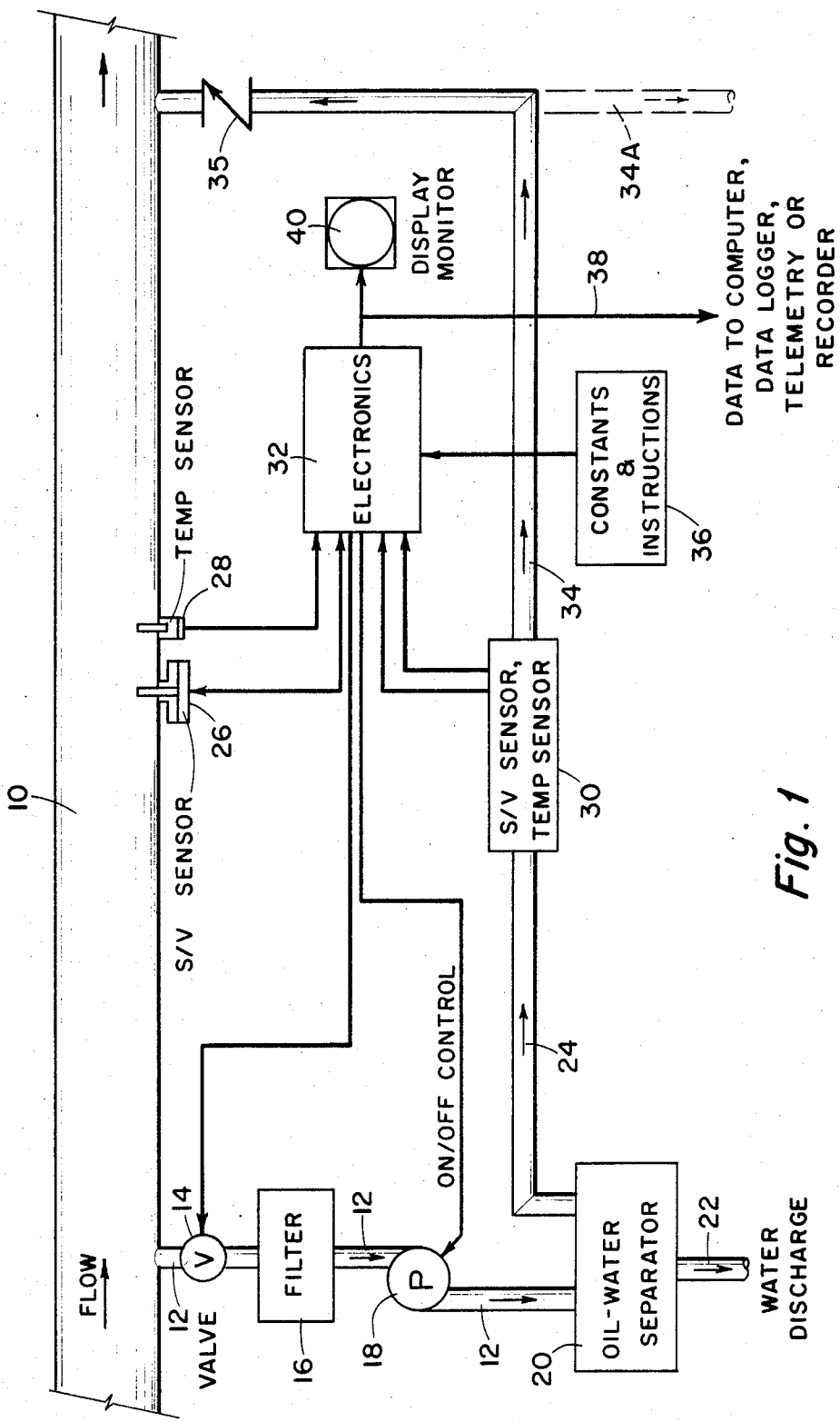
FIG. 1 is a diagrammatic illustration of the apparatus for practicing the method of this invention in a simplified version.

Referring to the drawings and first to FIG. 1, a simplified embodiment for practicing the invention is illustrated. A pipeline 10 carries a flow of an oil and water mixture. While the invention has a variety of applications it is primarily and specifically useful for measuring the water content of crude oil flowing in a pipeline 10. By means of a small conduit 12 and electrically operated valve 14 samples of the mixture flowing in the pipeline 10 can be taken. As will be described in more detail subsequently, the samples may be taken on a continuous basis but more preferably in practicing the invention are taken at periodic but frequent intervals.

Fluid passing through valve 14 flows through a filter 16 for removal of any solid contaminants which may be carried by the mixture.

From filter 16 the conduit 12 is connected with a pump 18. The use of pump 18 is optional as will be further illustrated. From pump 18 conduit 12 passes to an oil/water separator 20.

The specific configuration of the oil/water separator 20 is not a portion of the invention. Many types of such separators are known and are commercially available.

One type typically includes a cell wherein, through processes of coalescing, the water and oil are separated, the water being discharged through an outlet conduit 22 and the mixture sample having the water extracted therefrom, that is, the oil portion of the mixture, is carried away from the separator in conduit 24.

A sound velocity sensor 26 is connected to pipeline 10 preferably in conjunction with a temperature sensor or probe 28.

In like manner, a sound velocity and temperature sensor 30 are connected to measure the sound velocity and the temperature of the sample of the mixture having the water extracted from it (oil) in conduit 24. The measurements provided by instruments 26, 28 and 30 are fed through electronics 32 which also employs conductors for actuation of valve 14 and for the ON/OFF control of pump 18.

The mixture having the water extracted from it (oil) flows from the sensor 30 by way of conduit 34 and may return to the pipeline 10 by conduit 34 and check valve 35 as shown in solid outline. If it is not necessary or desirable that the sample having the water extracted from it be returned to the pipeline it may be discharged by alternate conduit 34A shown in dotted outline. Where it is desirable to return the sample of the fluid having the water extracted from it back to pipeline 10 the use of pump 18 is important, if not mandatory. However, if the conduit 34 is to connect to conduit 34A so that the fluid flowing therethrough is discharged into a sump, or any environment having a pressure below that of pipeline 10 then the use of pump 18 is not required. Generally speaking it is desirable that pump 18 be employed and that the fluid from conduit 34 flow back to the pipeline. In like manner, if there are no facilities for disposing of the water in discharge conduit 22 it could also connect back to the pipeline. It is important that conduit 34 connect to pipeline 10 downstream of the conduit 12 where the sample is taken and also downstream of sensors 26 and 28.

In electronics 32 the sensors 26, 28 and 30 are controlled and the measurements detected from these sensors are compared. By means of constants and instructions, which may be in the form of a computer program contained in the electronics of element 36 the measurements made by instruments 26, 28 and 30 are compared and the comparisons employed for determining the ratio of water to the oil content in the mixture flowing in the pipeline 10. Generally speaking, sound travels faster in water than in crude oil. Thus, the nearer the detected sound velocities by instruments 26 and 30 approach each other, the less water there is in the mixture flowing in pipeline 10. The temperatures of the fluids for which the speed of sound transmission is determined is highly important and therefore the temperatures are employed in the comparisons necessary for arriving at the ratio of the water to the oil content of the mixture.

The output from electronics 32 can be fed by conductor 38 to a multitude of further uses, such as to a computer, data logger, recorder or for telemetry to a central processing location. In addition, the output can be provided, as indicated, directly to a display monitor 40 so that the detected ratio of oil and water content flowing through the pipeline is displayed.

Figure 2:
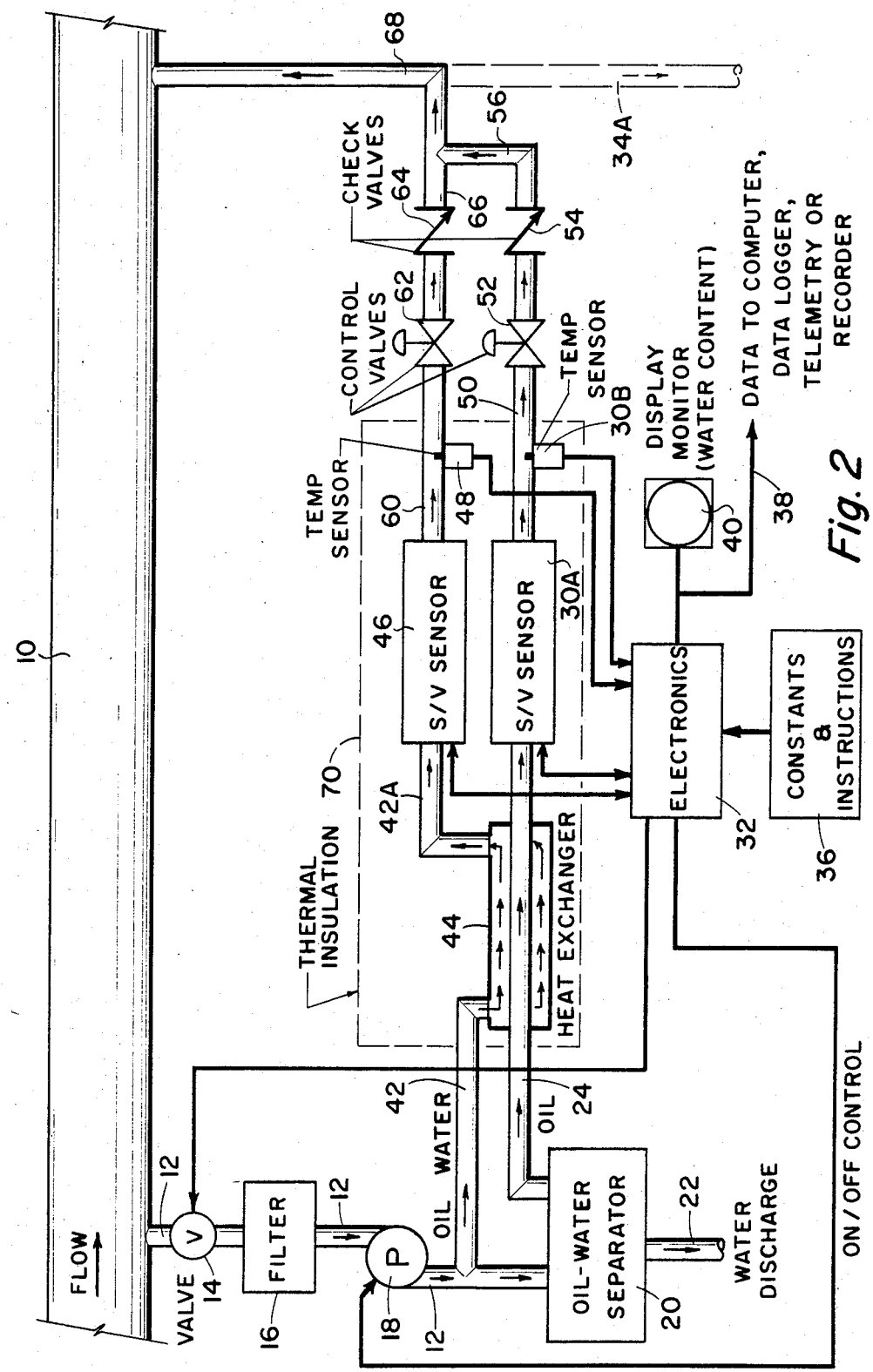
FIG. 2 is a diagrammatic illustration of the apparatus employed for practicing the method of this invention in a preferred embodiment.
Figure 5:
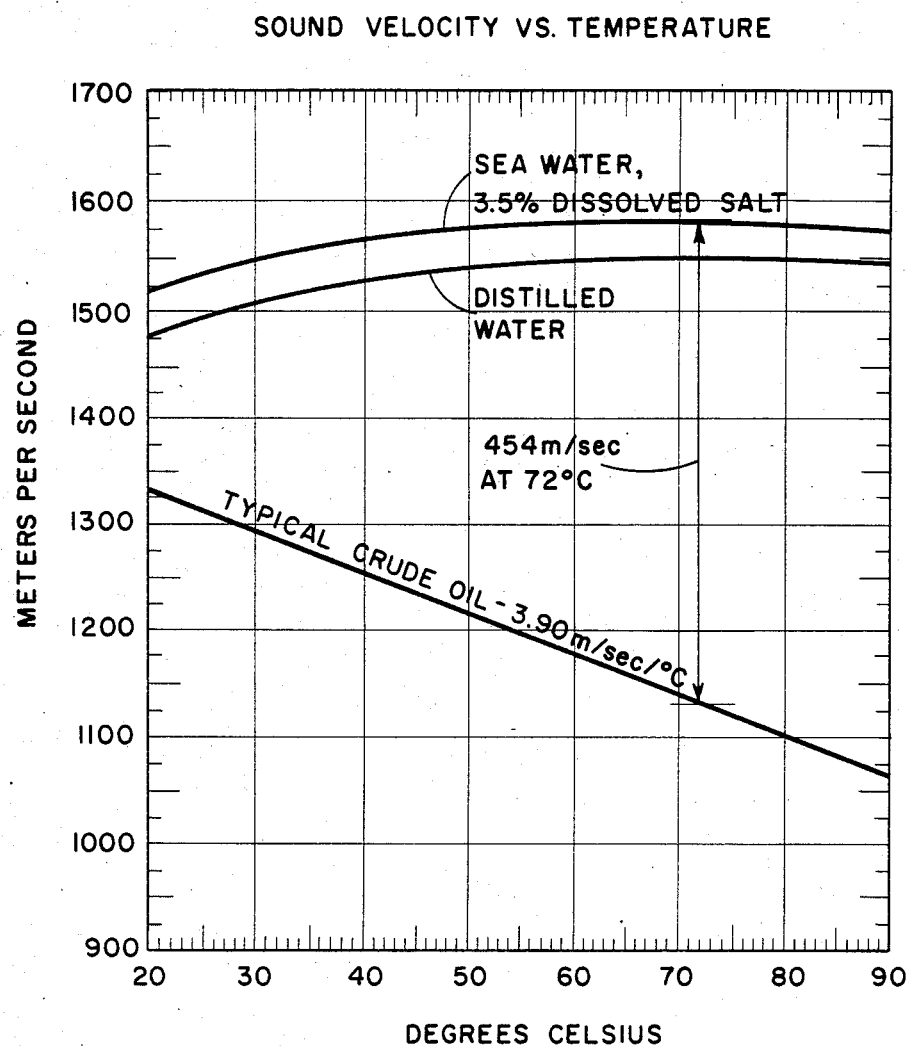
FIG. 5 is a plot of sound velocity versus temperature for sea water, distilled water and typical crude oil.

FIG. 2 is an alternate and preferred embodiment of the invention in which the elements having the same numbers as in FIG. 1 perform the same functions. In the embodiment of FIG. 2 the mixture flowing from pump 18 through conduit 12 is divided into two paths, the first path being to the oil/water separator 20 as in FIG. 1, the second path being conduit 42. Conduit 24 carries with it a mixture having the water extracted from it (oil) whereas conduit 42 carries the same mixture as that which flows through pipeline 10. As previously indicated temperature is very important in making speed of sound transmission measurements. For simplicity of circuitry and accuracy it is desirable that the measurements be made at the same temperature. For this reason, a heat exchanger 44 is employed in which the fluids flowing through conduits 24 and 42 are thermally interrelated without combining them. Also, the heat exchanger may be used to elevate the temperature of the incoming liquids to increase the difference in sound velocities and provide greater water measurement accuracy (see attached FIG. 4 from U.S. Pat. No. 3,973,430).

The mixture having the water separated therefrom, (oil) flows through a sound velocity and temperature measurement station 30A as in FIG. 1, except that in FIG. 2 the sound velocity sensor is separately indicated by the numeral 30A and the temperature probe by 30B. Elements 30A and 30B perform the same function as the sound velocity and temperature probe 30 of FIG. 1, with the outputs thereof being fed to electronics 32 in the same manner.

Conduit 42A conveys the mixture to a sound velocity sensor 46 and temperature probe 48.

From sound velocity sensor 30A and temperature probe 30B conduit 50 flows through a control valve 52 and a check valve 54 to conduit 56. In like manner, the fluid flowing from sensor 46 and temperature probe 48 flows by way of conduit 60 through a control valve 62 and check valve 64 to conduit 66. The flow from conduits 56 and 66 merge into conduit 68 which, in solid outline, is shown connecting back to pipeline 10. As described with reference to FIG. 1, if the sample fluid is to be returned to pipeline 10 the use of pipe 68 is necessary. However, if the sample fluid is to be discharged into a receptacle having pressure lower than that of the pipeline 10 the combined output from conduits 56 and 66 may be conveyed to such receptacle by discharge conduit 34A shown in dotted outline.

The arrangement of FIG. 2 is preferred since it provides improved opportunity for making measurements of the mixture compared to measurements of the mixture having the water extracted therefrom under substantially identical conditions and temperatures. In addition to employing heat exchanger 48, the sound velocity sensors 34A and 46, as well as the temperature probes 30B and 58 may be surrounded by insulation 78 so as to more completely insure that the measurements will be made under the same temperature conditions and at an elevated temperature for greater accuracy, if desired.

FIG. 3 is an enlarged view of a portion of the apparatus as employed in FIG. 2 of the invention. FIG. 3 shows the arrangement wherein the sound velocity sensors 30A and 46 are each of the type utilizing a single transducer and sound reflector. Sound velocity sensor 46 includes housing 72 and sound velocity sensor 30A includes housing 74. Housings 72 include a piezo electric crystal element indicated, in FIG. 4, by the numeral 76, the crystal element being shown in dotted outline since it is normally concealed behind a transducer window and is not directly subject to contact by the fluid for which the speed of sound of transmission is being measured. Extending from the housing 72, as shown in FIGS. 4, are spacers 78 which support a sound reflector 80 at a preselected distance away from housing 72. The speed of sound transmission is made by measuring the travel time for transmission of the sound from the transducer window until it is received again by the transducer from the reflector 80. The sound velocity sensor 30A is similarly constructed.

The transducer housing 72, spacers 78 and reflector 80 are contained within a fluid tight chamber 82 so that fluid flowing from conduit 42A flows freely in the space between the spacers 78. The same arrangement is employed in conjunction with the transducer housing 74, the containment vessel being identified by the numeral 84.

Since the difference in the speed of sound transmission of oil and water is greater as the temperature of these fluids increase, it may be desirable in the arrangement of FIG. 2 to provide a preheater such as in conjunction with heat exchanger 44 to increase the temperature of the fluids being measured to such as between 50° to 70° C.

When separating water from crude oil in order to prepare a reference liquid for the differential sound velocity measurement, it is important that the preparation time be short compared to the time during which the sound velocity of the oil itself may change. In other words, the sampling and measurement rate must be fast compared to the rate of change of sound velocity of the crude oil. When the crude oil is supplied from a single source such as a tanker or from a single well or family of wells, the sound velocity of the oil should change slowly and perhaps no greater than 0.1 meter per second during the time that a sample is taken, separated and measured. When taking samples periodically from a flowing crude oil line, the specific gravity and, hence, the sound velocity of the crude may change rapidly if the feed to the line is diverted from one well or set of wells to another well or set of wells. When such a diversion occurs and is accompanied by a change in sound velocity of the oil, it is essential that sampling and measurement be conducted often enough so that measurement of water in oil will essentially be continuous and free of significant measurement error.

The velocity of sound of any hydrocarbon decreases linearly as its temperature increases. Therefore, it is a relatively simple matter to compensate for temperature changes provided that the temperature coefficient of the crude oil is known. This may be determined in advance and programmed into the instrument or the instrument can be designed to automatically determine the temperature coefficient by withdrawing a sample from the crude oil line and making sound velocity measurements at two different temperatures. This would involve a heat exchanger which would be under the control of a microprocessor whereby the temperature of the crude oil would be adjusted in a controlled fashion to one temperature followed by a measurement of sound velocity and then to a second temperature followed by a second sound velocity reading. This procedure would be valid for water content up to perhaps 10 or 15 percent. If larger amounts of water are present in the oil, then it would be necessary to take readings of sound velocity continuously over the entire temperature range while the heat exchanger is altering the temperature of the sample so that a second order correction could be made for temperature. Stated another way, when appreciable amounts of water are present in the oil, the relationship between sound velocity and temperature would be curvilinear rather than perfectly linear with the amount of curvature increasing with water content. If automatic temperature change of the incoming sample is not feasible such as when employing a simplified system (FIG. 1), then it may be necessary to program both the first order and second order temperature coefficients into the electronics so that a curvilinear correction can be applied to the sound velocity measurement of oil and water. Only a linear correction to the sound velocity measurement of water-free oil would be necessary.

The invention provides an easily portable and extremely compact system for monitoring the amount of water being conveyed in a crude oil pipeline, although the application of the invention is not limited to this specific purpose.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A method of measuring the composition of an oil and water mixture flowing in a pipeline comprising:
   (1) extracting a sample of mixture from the pipeline;
   (2) measuring the speed of sound transmission of the mixture;
   (3) measuring the temperature of the mixture;
   (4) separating the water from the sample;
   (5) measuring the speed of sound transmission of a sample having the water separated therefrom;
   (6) measuring the temperature of the sample having the water separated therefrom; and
   (7) comparing the determined speed of sound transmission of the mixture and the speed of sound transmission of the sample having the water separated therefrom as corrected for the detected temperatures to determine the ratio of oil and water in the mixture.

2. The method of claim 1 wherein said sample is taken on a periodic basis and wherein steps (2), (3), (5) and (6) are carried out substantially concurrently.

3. The method of claim 1 including, after step (6), returning the sample having the water separated therefrom to the pipeline.

4. The method of claim 3 wherein the step of returning the sample having the water separated from the pipeline includes returning the sample having the water separated therefrom to the pipeline downstream of the location wherein steps (1) and (2) are carried out.

5. The method of claim 1 wherein step (2) is carried out in the pipeline.

6. The method of claim 1 wherein steps (2) and (3) are carried out in the pipeline.

7. The method of claim 1 wherein step (2) is carried out in at least a portion of the extracted sample of the mixture.

8. A method of measuring the composition of an oil and water fluid mixture flowing in a pipeline comprising:
   (1) extracting a sample of the mixture;
   (2) separating the water from the sample;
   (3) separately and substantially simultaneously measuring the speed of sound transmission of the fluid mixture flowing in the pipeline and in the sample having the water separated therefrom obtained in step (2); and (4) comparing the determined speed of sound transmission of the mixture flowing in the pipeline with that of the sample having the water separated therefrom to determine the ratio of oil and water in the mixture flowing in the pipeline.

9. The method of claim 8 including:

(5) in step (3) measuring the temperature of the fluid mixture in the pipeline and of the sample having the water separated therefrom;

(6) employing the detected temperatures in step (4).

* * * * *